US007540863B2

(12) United States Patent
Haindl

(10) Patent No.: US 7,540,863 B2
(45) Date of Patent: Jun. 2, 2009

(54) MEDICAL TRANSFER DEVICE

(76) Inventor: Hans Haindl, Georgsplatz 1, 30974 Wennigsen (DE)

( * ) Notice: Subject to any disclaimer, the term of this patent is extended or adjusted under 35 U.S.C. 154(b) by 144 days.

(21) Appl. No.: 11/497,242

(22) Filed: Aug. 2, 2006

(65) Prior Publication Data

US 2007/0088315 A1 Apr. 19, 2007

Related U.S. Application Data

(63) Continuation of application No. PCT/EP2005/001117, filed on Feb. 4, 2004.

(30) Foreign Application Priority Data

Feb. 4, 2004 (DE) ...................... 10 2004 005 435

(51) Int. Cl.
*A61B 19/00* (2006.01)

(52) U.S. Cl. ........................ 604/414; 604/415; 604/413

(58) Field of Classification Search ......... 604/414–416, 604/905
See application file for complete search history.

(56) References Cited

U.S. PATENT DOCUMENTS 4,576,211 A 3/1986 Valentini et al.
4,759,756 A * 7/1988 Forman et al. .............. 604/413
5,342,346 A * 8/1994 Honda et al. ................ 604/413
5,445,631 A * 8/1995 Uchida ....................... 604/412
5,478,337 A * 12/1995 Okamoto et al. ............ 604/413
6,070,623 A 6/2000 Aneas
6,258,078 B1 7/2001 Thilly
6,558,365 B2 5/2003 Zinger et al.
6,571,837 B2 * 6/2003 Jansen et al. ................ 141/329
2001/0003996 A1 6/2001 Jansen et al.
2002/0087141 A1 7/2002 Zinger et al.

FOREIGN PATENT DOCUMENTS

DE 699 03 266 T2 6/2003

* cited by examiner

*Primary Examiner*—Leslie R Deak
(74) *Attorney, Agent, or Firm*—Shlesinger, Arkwright & Garvey LLP

(57) ABSTRACT

Medical transfer device conducts fluid from a container to a bottle having a neck, which has a closing element pierceable by a needle. Transfer device includes a first tubular-shaped part telescopically displaceable in a second tubular-shaped part between an inserted position and an extracted position. A holding part is provided inside first tubular-shaped part. A cannula extends from holding part into second tubular-shaped part without axially overlapping into the extracted position. Cannula includes a lateral opening on its distal end. Conical-shaped receiving element connects a detachably sealed connection of conical-shaped receiving elements with the container, and is connected to the inside of the cannula in the holding part. The tubular-shaped parts are detachably locked by locking tongues, so that the tip of the cannula is located inside the tubular-shaped part, avoiding injury risk. Rotation of the tubular-shaped parts determines penetration depth of the tip of the cannula in the bottle.

18 Claims, 6 Drawing Sheets

MEDICAL TRANSFER DEVICE

CROSS-REFERENCE TO RELATED APPLICATIONS

This application is a continuation of application no. PCT/EP2005/001117, filed Feb. 4, 2004, which claims the priority of German application no. 10 2004 005 435.5, filed Feb. 4, 2004, and each of which is incorporated herein by reference.

FIELD OF THE INVENTION

The invention relates to a medical transfer device. More particularly, the invention relates to a medical transfer device of the type for transferring fluid from a container into a bottle. Even more particularly, the invention relates to a medical transfer device of the type including a cannula for transferring fluid from a container into a bottle, the neck of which bottle includes a pierceable closing element, and the removal of the transferred fluid moved into the bottle.

BACKGROUND OF THE INVENTION

Numerous medications cannot be stored in liquid form, but have to be dissolved in sterile water or another type of solvent before being used. It has been known for some time to on the one hand prepare a medication as a dry substance and on the other hand a solvent in separate injection bottles. The latter are closed with a closing element that can be penetrated by an injection needle. When using this, the closing element of the bottle containing the water is pierced with a steel cannula placed on top of a syringe and the water then extracted into the syringe. After pulling out the steel cannula it is entered into a closing element of a bottle, which contained the medication as a dry substance, and the water is fed into this bottle from the syringe. Afterwards the bottle is shaken until the medication has dissolved and the dissolved medication is drawn into the syringe with the same cannula. This procedure is relatively elaborate and dangerous due to operation of the steel cannula.

U.S. Pat. No. 6 558 365 B2 discloses a medical transfer device consisting primarily of two caps, each bottom of which contains one spike extending into the inner part of the cap. The outer surface of one of the caps has a pin with a conical outer surface, extending into a conical recess of a pin placed on the bottom of the other cap. A connection canal runs through the spikes and the pins. The cylindrical parts of the caps are split and can therefore be widened radially in such a way that each of the caps can be snapped open across the bulge of the neck of a bottle. The length of the spikes is selected so that the closing element of the bottle is pierced during this process. First, one of the caps is snapped onto the neck of a bottle containing either water or another solvent, so that the appropriate spike pierces the closing element of the bottle and reaches the inside of the bottle. Then, the other cap is snapped onto the neck of a bottle containing a medication in the form of a dry substance. Afterwards, both caps are connected to one another by their spikes. Then the fluid is filled into the bottle with the dry substance and the latter dissolved in the fluid. Then the cap belonging to the bottle with the dissolved medication is removed, so that the complementary conical pin of a syringe can be inserted into the conical receiving element of the other cap and the medication can be extracted.

However, this known design has several disadvantages. One of the disadvantages is that the caps could be mistakenly switched when placed on the necks of the bottles, creating the danger that the cap with a conical pin will remain on the bottle with the dissolved medication, which pin provides no connection with the conical pin of a syringe, and the medication cannot be extracted. Afterwards a cannula has to be placed on the syringe, which can lead to injuries caused by the tip of the cannula, particularly when the patient is administering the injection, which is most often the case.

U.S. Pat. No. 6 070 623 discloses a medical transfer device with a first tubular-shaped part that is movable inside of a second tubular-shaped part between an inserted and extracted position. A holding part is connected to the first tubular-shaped part and has a conical receiving element for connecting means for detachable and sealed connection of the conical receiving element with a container holding the fluid or rather the solvent. It is formed by a syringe featuring a cylindrical wall and a movable rod inside of it, which is movable by means of a piston rod.

There is a cannula on the opposite side of the conical receiving element on the second tubular-shaped part, through which a canal extends from the inner side of the conical receiving element to its tip.

During usage of this known device, first sterile water or a sterile solution is drawn up and the anterior conical pin of the needle is placed in the conical receiving element in the first tubular-shaped part. Afterwards, the second tubular-shaped part is placed on the neck of a bottle containing a dry, powder-shaped medication and featuring a pierceable closing element and the cannula of the syringe pierces the closing element of the bottle containing the medication. Then, by using the syringe, the fluid inside of the syringe is injected into the container containing the medication and the medication is dissolved in the fluid. The container with the medication is at the bottom and the syringe at the top during this process; the device is turned upside down in a way that the fluid containing the medication is above the spike, so that fluid containing the medication can be extracted by the syringe. Then the connective pin of the syringe is separated from the conical receiving element of the first tubular-shaped part and an injection syringe is placed on the connective pin of the needle, so that the medication can be injected into the body of a patient. Attaching the injection needle can lead to injuries caused by the tip of the needle, just as with the first device, particularly when the patient is administering the injection, which is most often the case. Also, another disadvantage is that the penetration depth of the cannula during injection and extraction of the fluid depends on how it is handled.

OBJECTS AND SUMMARY OF THE INVENTION

An object of the invention is to provide a medical transfer device of the type including a cannula for transferring fluid from a container into a bottle, the neck of which bottle includes a pierceable closing element, and the removal of the transferred fluid moved into the bottle with a cannula, which avoids the disadvantages of the known devices, which is therefore easy to use, and decreases or eliminates the danger of injuries caused by pointed parts.

This object of the invention is achieved by the teachings according to the invention set forth herein.

A fundamental object of the invention is to place the pointed cannula necessary for piercing the closing element of the bottle containing the medication between two tubular-shaped parts, which are movable in a telescope-like manner between an inserted and extracted position. On the inner side of the first tubular-shaped part there is a holding part connected to this, from which the cannula extends into the inner part of the second tubular-shaped part without projecting above it axially. The posterior end of the cannula is connected with a conical receiving element which is on the holding part on the opposite end of the cannula. Both tubular-shaped parts are prevented from moving towards one another by a locking mechanism in the extracted position, so that the tip of the cannula is inside of the tubular-shaped parts, avoiding any danger of injury.

An important fundamental object of the teaching according to the invention is to guarantee that the fluid discharges from the lateral opening at the tip of the cannula aimed laterally at the lateral inner wall of the bottle when the cannula protrudes into the bottle after the cannula has pierced the closing element. The advantage of this is that the fluid runs down along the inner wall of the bottle and reaches the medication along the entire inner circumference of the bottle so that the fluid can effectively admix with the medication. A disadvantage would be that not all of the fluid can be withdrawn from the bottle since the lateral opening at the tip of the cannula does not protrude into the bottom part of the bottle containing the fluid next to the closing element after the transfer device is turned over. For this reason the invention also provides for the cannula to be pulled back to a stopper after injection of the fluid so that the lateral opening of the cannula is located immediately in front of the closing element in the injection direction.

According to another embodiment of the invention there is a pin on the inner wall of the second tubular-shaped part while there are two grooves connected by a switch on the outer wall of the first tubular-shaped part in the injection direction. The pin is located in the grooves and slides into one of the two grooves from inserted to extracted position and in direction of the extracted position through the switch into the other groove during subsequent movement until it locks in place in a recess and is thereby locked in this position. It is guaranteed in this position that the lateral opening at the tip of the cannula is located right above the closing element so that all of the fluid can be withdrawn from the container.

So there are a total of three positions with this embodiment. The two tubular-shaped parts are locked together by a locking device in the first position. After releasing this locking device the cannula can be inserted deeply enough into the bottle containing the medication, while the lateral opening at the tip of the cannula is located immediately next to the closing element in the third position.

Another embodiment in accordance with the invention includes in it that the different positions are reached by turning the two tubular-shaped parts. In this embodiment of the transfer device according to the invention there is a pin on the outer wall of the first tubular-shaped part, while there are two grooves on the inner wall of the second tubular-shaped part in the injection direction; they are connected with one another by a switch, and the pin is located in the grooves, sliding into one of the two grooves from an extracted into an inserted position and through the switch into the other groove to a stopper in direction of extracted position during subsequent movement, so that the cannula protrudes from the second tubular-shaped part in a desired manner and therefore into the bottle immediately adjacent the pierceable closing element. Of course it is also possible with this embodiment that the pin is located on the inner wall of the second tubular-shaped part and the grooves in the outer wall of the first tubular-shaped part.

According to a further embodiment of the invention the end opposite to the tip of a spike engages tightly with the conical receiving element and so connects it with a container containing the fluid when the spike has pierced the closing element of the container containing the fluid.

Functionally, the end of the spike opposite to the tip is conical complementary to the conical receiving element in the holding part, so that a firm connection is possible.

According to another embodiment of the invention the end of the spike opposite to the tip is placed in the holding part cylindrically or conically with a conical angle, which is smaller than the conical angle of the conical receiving element. In this manner, too tight clamping of the spike in the conical receiving element is avoided, so that the spike can be removed without using too much strength, and the usual conical pin of a syringe can be affixed on the conical receiving element.

Advantageously, there are clamps from the end of the second tubular-shaped part opposite to the first tubular-shaped part for engaging a bulge at the end of a bottle neck. These clamps enable centered placing on the bulge of a bottle and therefore also centered placing of the spike in the pierceable closing element of a bottle.

It is also advantageous in the same manner that clamps extend from the end of the first tubular-shaped part opposite to the second tubular-shaped part for engaging a bulge at the end of a bottle neck. This guarantees centered placing of the transfer device according to the invention and centered piercing of the pierceable closing element by the cannula. The bottles with the solvent and the medication as dry substance are interlocked because there are clamps on both tubular-shaped parts in these embodiments.

According to an advantageous embodiment of the invention the spike is held in the center of a plate, which is supported by the first tubular-shaped part opposite to injection direction, which makes removal of the spike easier.

Another advantageous embodiment of the invention is that the plate include clamps for engaging a bulge at a bottle neck; in doing so these clamps extend between the gaps formed by the clamps of the first tubular-shaped part in circumferential direction and also engage the same bulge of a bottle neck. The first tubular-shaped part and the plate with the spike can therefore be placed onto the bottle independently of one another.

In an especially advantageous embodiment of the invention the clamps of the plate have stronger holding force than the clamps of the first tubular-shaped part, in such a manner that when removing a bottle from the first tubular-shaped part the plate with the spike is also removed and remains attached to the bottle. In this way the conical receiving element connected to the cannula is disconnected so that the conical pin with a syringe can be put on and the dissolved medication can be suctioned off.

In accordance with another embodiment of the invention, the spike is made of synthetic material. Advantageously, the cannula is provided with a lateral opening, which decreases or eliminates the risk of clogging by punched out parts of the pierceable closing element and has the particular advantage that the water jet discharges laterally and wets the bottle's wall, which leads to better and foam-free dissolution of the dry substance. Functionally, the cannula is made of steel and can be furnished with a filter in the conical receiving element or in the end opposite to the tip of the spike. The spike and/or the cannula can advantageously be configured as double spikes, or rather double cannulas, each featuring a channel as an aeration or ventilation channel.

Relative terms such as up, down, left, and right are for convenience only and are not intended to be limiting.

DETAILED DESCRIPTION OF THE INVENTION

Figure 1:
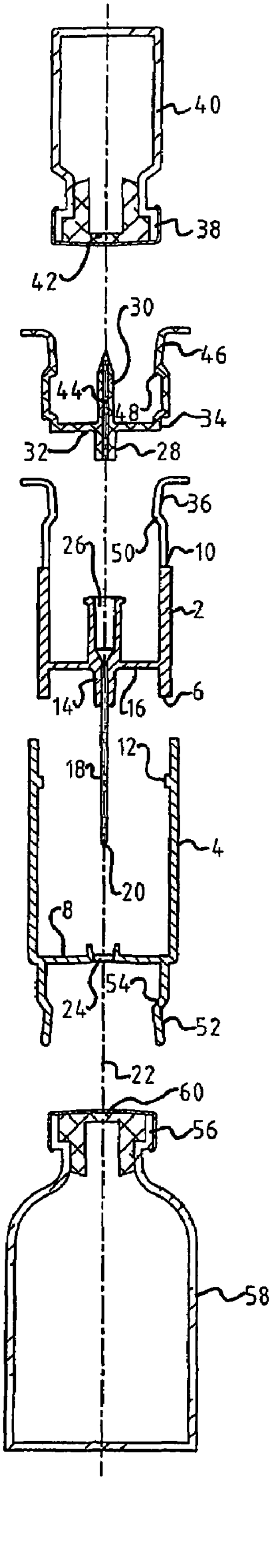
FIG. 1 shows an axially exploded view of an embodiment of a transfer device according to the invention connected to two bottles, shown in axial section.

FIG. 1 shows a first tubular-shaped part 2, which is telescopically movable inside of a second tubular-shaped part 4 between an inserted position, in which an edge 6 of the first tubular-shaped part pushes against a wall 8 of the second tubular-shaped part, and an extracted position, in which an edge 10 of the first tubular-shaped part 2 pushes against a pin 12 on the inner wall of the tubular-shaped part 4. There is a holding part 14 inside of the first tubular-shaped part 2, which is connected to the first tubular-shaped part 2 by a disc-shaped bar 16. The bar 16 includes predetermined breaking points, which are not shown, so that the holding part 14 can be broken out from the interior of the first tubular-shaped part 2. The holding part 14 holds the back end of a cannula 18, the tip 20 of which is positioned along an axis 22 and directed toward a recess 24 in the wall 8. When assembled, the inner channel of the cannula 18 is connected with a conical receiving element 26, which engages tightly with the cylindrical back end 28 of a spike located in the center of a plate 32, an edge 34 of which, when assembled, supports an edge 10 in an opposite direction to the injection direction.

There are clamps 36 extended from the edge 10 of the tubular-shaped part 2, which engage a bulge 38 of a bottle 40 when the pierceable closing element or closure 42 of the bottle 40 is pushed against the spike 30, so that its interior channel 44 is connected with the interior of the container 40. Thus, the interior of the container 40 is also connected with the tip 20 of the cannula 18.

There are gaps between the clamps 36 in a circumferential direction, which are not visible in the drawing and into which, when put together, clamps 46 protrude; these clamps 46 engage the container 40 in the same way as clamps 36 engage the bulge 38. Clamps 46 include slopes 48, which are steeper than embankments 50 of the clamps 36, so that the holding force of clamps 46 with their embankments 48 is stronger than that of clamps 36 with their embankments 50, with the consequence that the clamps 46, plate 32, and spike 30 get snagged on the bulge 38 and are also removed by container 40 when it is removed.

There are guide clamps 52 on the opposite side of tubular-shaped part 2 on the second tubular-shaped part 4, which with their embankments 54 engage a bulge 56 on the bottle neck 58 and so guarantee central positioning of the second tubular-shaped part 4 relative to the bottle 58, so that when the first tubular-shaped part 2 moves the cannula 18 pierces the closing element 60 of the bottle 58 centrally, so that finally the interior of the bottle 58 is connected with the interior of container 40 by the cannula 18, the conical receiving element 26, and the interior channel 44 of the spike 30. In practice, there is a medication as dry substance in bottle 58, while container 40 holds a solvent, usually water. When assembled, the tubular-shaped parts 2 and 4, and the spike 30, and the parts connected to them constitute a medical transfer device according to the invention.

FIGS. 2 to 15 explain the use of the transfer device in greater detail. FIGS. 2 to 15 generally only provide basic parts with the reference numbers from FIG. 1 for reasons of clarity.

Figure 2:
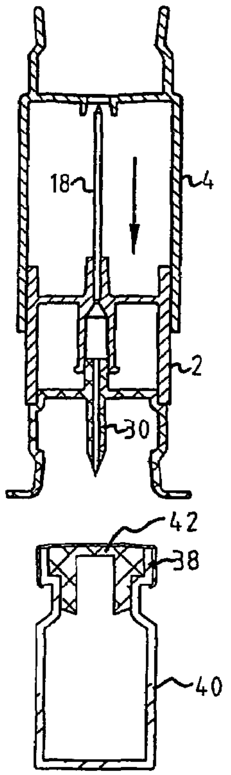
FIGS. 2 to 15 illustrate use of the transfer device of FIG. 1.
Figure 3:
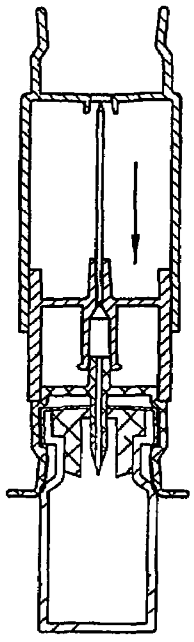
Figure 6:
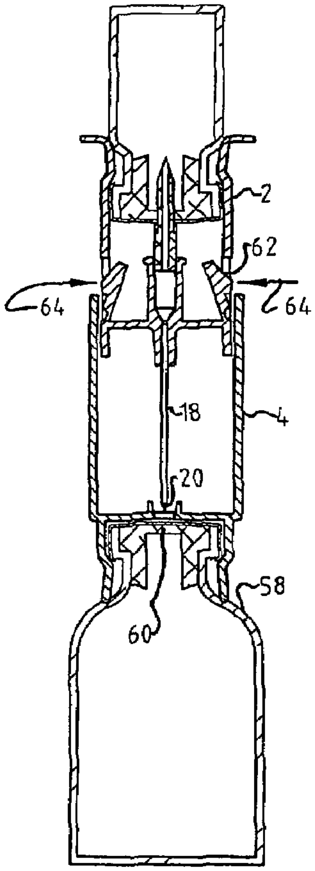
Figure 7:
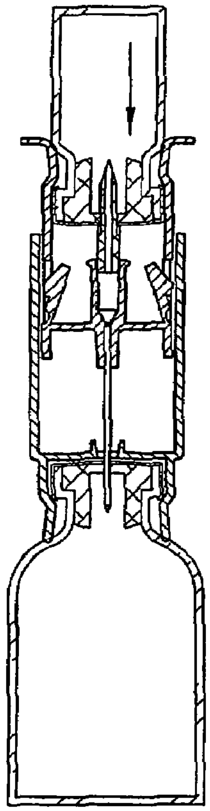

FIG. 2 shows the transfer device put together with the tubular-shaped parts 2 and 4 in an extracted position, being locked by impressible waling connecting plates 62, which are explained in greater detail in FIGS. 6 and 7, against axial movement towards one another. In this position the tips of cannula 18 and of the spike 30 are inside of the tubular-shaped 2 and 4, so that there is no danger of injury. The transfer device is then pushed up against container 40 from above, so that the spike 30 pierces the closing element 42 and the clamps 36 and 46 engage the bulge 38. This state is illustrated in FIG. 3.

Figure 4:
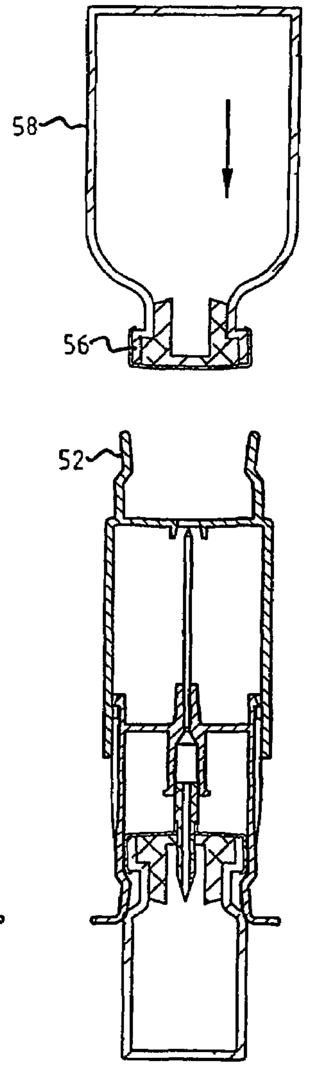
Figure 5:
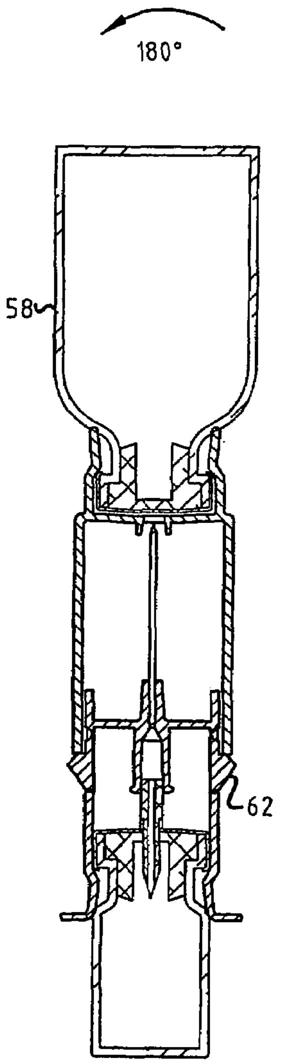

After that, according to FIG. 4, the bottle 58 containing a medication as dry substance is moved downward in direction of the guide clamps 52 until they snap behind the bulge 56 of the bottle 58 and keep them centered. This state is shown in FIG. 5, however illustrated by one rotation around its axis, differentiating from FIG. 4, so that the impressible connecting plates 62 are visible.

Figure 8:
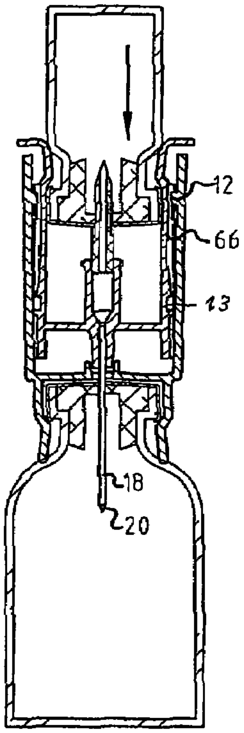

After that, the entire device according to FIG. 6 is turned upside down, whereby the connecting plates 62 are impressed in the direction of the arrows 64, so that the first tubular-shaped part 2 is movable downward into the second tubular-shaped part 4 with the consequence that the tip 20 of the cannula 18 pierces the closing element 60 and is thereby connected with the interior of the bottle 58. This process is clarified in FIG. 7. At the end of this movement the position of the tip 20 of the cannula 18 is as shown in FIG. 8. In this position the fluid discharges from the lateral opening in the cannula 18, which is not visible in the drawing because of its small size, towards the inner lateral wall of the bottle 58 and along the wall to the bottom of the bottle 58 containing the dry medication, which is then dissolved.

Figure 9:
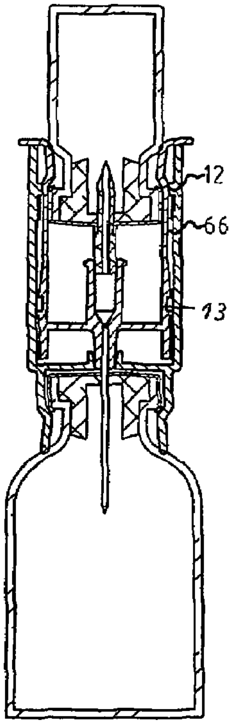
Figure 10:
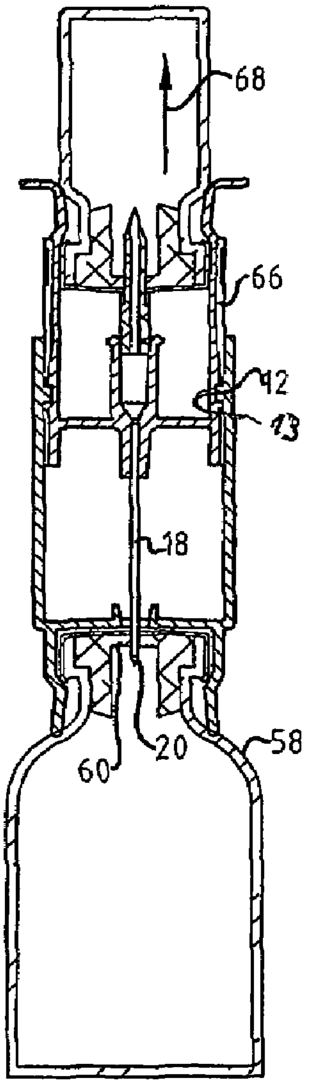
Figure 11:
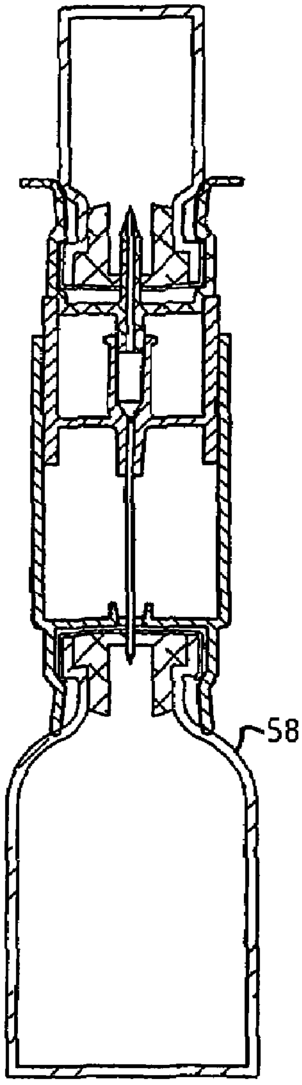
Figure 12:
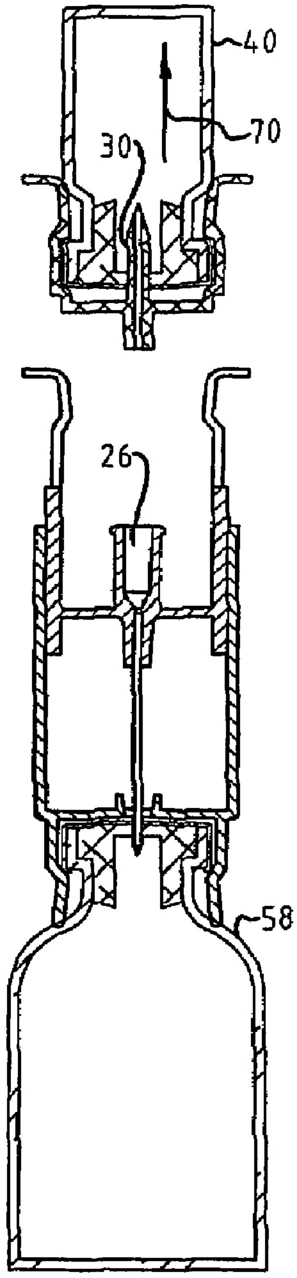
Figure 13:
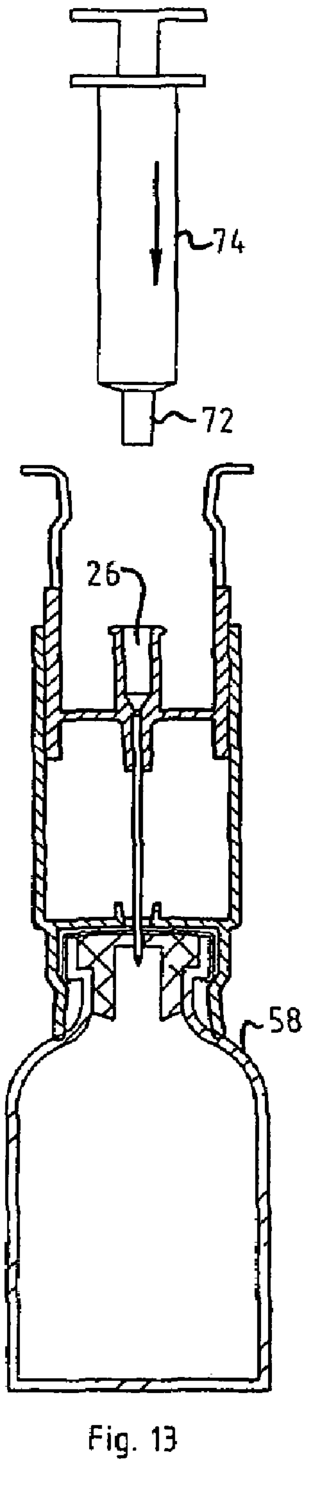
Figure 14:
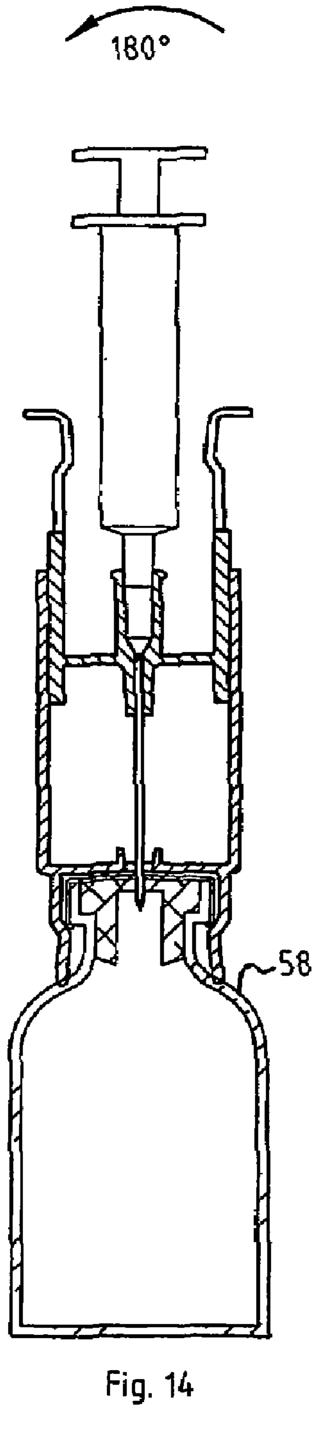
Figure 15:
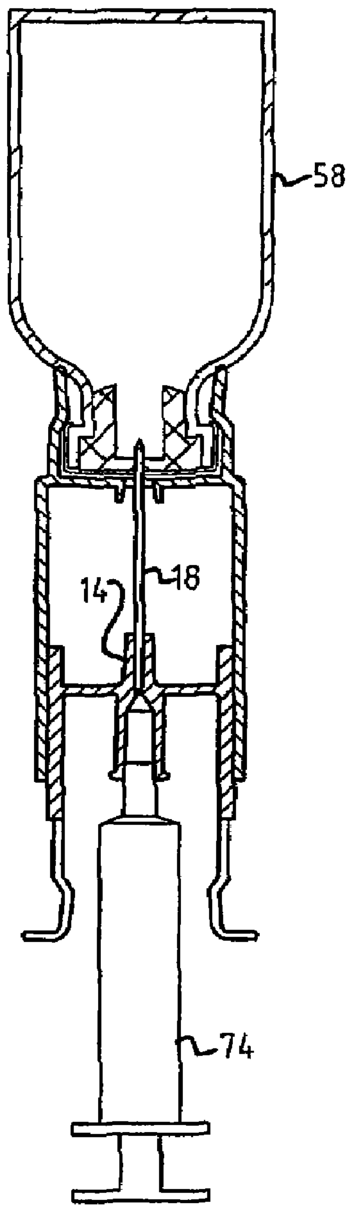

Since a medication can not be extracted into a syringe with the opening on the tip 20 in that position, the cannula 18 has to be moved back to a position shown in FIG. 10, where the opening on the tip 20 protrudes into the interior of the bottle 58 through the closing element 60. In order to accomplish this safely there are two grooves 66 extending in the axial direction in the outer wall of the first tubular-shaped part 2 in which the pin 12 engages, so that it slides into one of the grooves 66 when inserting the first tubular-shaped part 2, as shown in FIGS. 8 and 9, and, when extracting, from one of the grooves 66 into the other groove 66, where it catches in a recess 13 and so works as a stopper against movement in the direction of an arrow 68, thereby guaranteeing that the opening at the tip 20 of the cannula 18 remains fluidly connected with the interior of the bottle 58. In this position pin 12 is locked and cannot move any further. FIG. 11 shows this position after rotating the transfer device around its axis by 90°. Now, in accordance with FIG. 12, the container 40 and the spike 30 are moved upward in the direction of an arrow 70, so that the conical receiving element 26 is released and, according to FIG. 13, a conical tip 72 of a syringe 74 can be attached, as illustrated in FIG. 14. Afterwards the entire device is rotated, so that the medication in the position shown in FIG. 15 can be extracted from the bottle 58 into the syringe 74. After removing the syringe an injection needle can be placed on tip 72 in the usual fashion.

Instead of container 40, and likewise omitting spike 30, the conical pin in the conical receiving element 26 can be attached to a syringe filled with fluid and the fluid injected through the lateral wall at the tip 20 of cannula 18 against the inner wall of the bottle 58. Then, one proceeds according to FIGS. 13 to 15. Spike 30 may be made of synthetic material, and cannula 18 may be made of steel.

Figure 16:
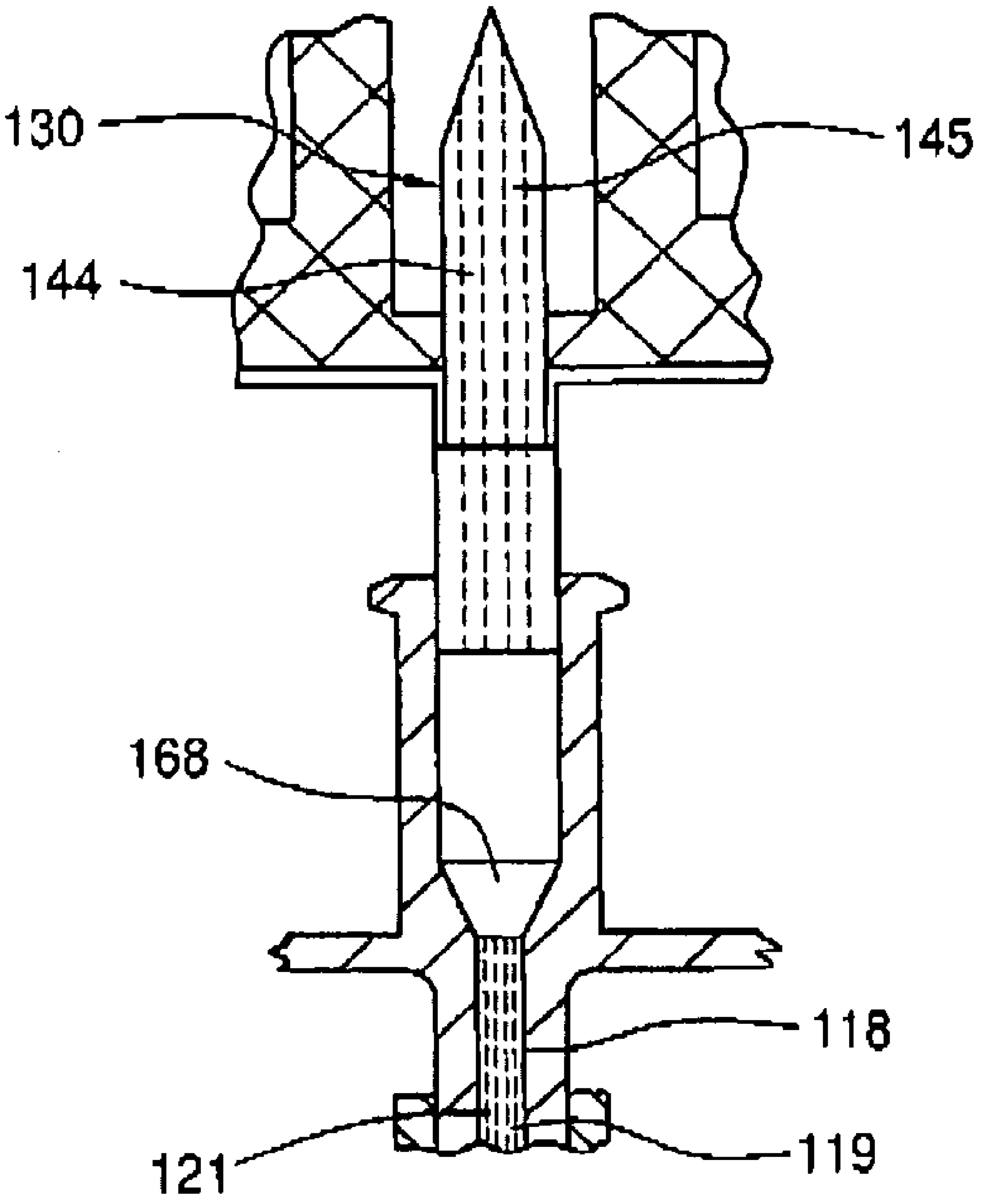
FIG. 16 shows an enlarged exploded view of another embodiment of a transfer device according to the invention.

FIG. 16 shows an enlarged exploded view of another embodiment of a transfer device according to the invention including a spike 130, and one of the conical receiving element 26 and the end opposite to the tip of the spike 130 may include a filter 168, as shown in F*ig*. 15, for example. Functionally, the cannula 118 is made of steel and can be furnished with a filter in the conical receiving element or in the end opposite to the tip of the spike, Spike 130 and/or the cannula can advantageously be configured as double spikes, or rather double cannulas, each featuring a channel as an aeration or ventilation channel, That is, spike 130 may include a channel 144 and 145, and cannula 118 may include a respective channel 119 and 121 as an aeration or ventilation channel.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention or limits of the claims appended hereto.

The invention claimed is:

1. Medical transfer device for transferring fluid from a container into a bottle, the neck of which bottle includes a pierceable closing element, and the removal of the transferred fluid moved into the bottle, the medical transfer device comprising:

a) a first tubular-shaped part which is telescopically movable in a second tubular-shaped part between an inserted and an extracted position;

b) a holding part connected with the first tubular-shaped part, the holding part including a conical receiving element to attach an element for releasable and sealable connection of the conical receiving element with the container containing the fluid;

c) a cannula connected with the interior of the conical receiving element and extending from the holding part into the interior of the second tubular-shaped part without extending axially past the second tubular-shaped part in the inserted position for withdrawing fluid transferred into the bottle;

d) a locking mechanism provided for tight locking of the two tubular-shaped parts in the inserted position;

e) the cannula including a lateral opening at its distal end, from which opening the fluid discharges laterally towards a lateral internal wall of the bottle, in use, when the cannula protrudes into the bottle after piercing the closing element; and f) the two tubular-shaped parts being rotatable against each other through a sufficiently limited angle, so that the first tubular-shaped part is movable into the extracted position after opening the locking mechanism in one rotated position, in which the cannula extends out of the second tubular-shaped part and protrudes through the closing element so far into the interior of the bottle attached to the second tubular-shaped part that the lateral opening in the cannula is facing away from the closing element in the injection direction, while the first tubular-shaped part is sufficiently retractable in another rotated position so that the lateral opening of the cannula is directly in front of the closing element in the injection direction.

2. Medical transfer device according to claim 1, wherein:

a) a pin is provided on the internal wall of the second tubular-shaped part;

b) two grooves are provided on the outer wall of the first tubular-shaped part, which are connected by a switch and in which the pin is located; and c) the pin is slidable into one of the two grooves from the inserted to the extracted position and into the other groove through the switch until it catches in a recess and is thereby locked in this position during subsequent movement in the direction of the extracted position.

3. Medical transfer device according to claim 1, wherein:

a) a spike having an end and a tip is provided; and b) the end is opposite to the tip of the spike and engages tightly with the conical receiving element, thus connecting the conical receiving element with a container containing the fluid when the spike has pierced the pierceable closing element of the container containing the fluid, in use.

4. Medical transfer device according to claim 3, wherein:

a) the end opposite to the tip of the spike is shaped conically complementary to the conical receiving element in the holding part.

5. Medical transfer device according to claim 3, wherein:

a) the end of the spike opposite to its tip is one of cylindrical and conical with a conical angle that is smaller than the conical angle of the conical receiving element in the holding part.

6. Medical transfer device according to claim 1, wherein:

a) the end of the second tubular-shaped part opposite the first tubular-shaped part includes clamps for releasably engaging a bulge at the end of the bottle neck, in use.

7. Medical transfer device according to claim 1, wherein:

a) the end of the first tubular-shaped part opposite the second tubular-shaped part includes clamps for engaging a bulge at the end of the neck of the container containing the fluid in use.

8. Medical transfer device according to claim 3, wherein:

a) the spike is located at the center of a plate, which is supported by the first tubular-shaped part opposite to the injection direction.

9. Medical transfer device according to claim 8, wherein;

a) the plate includes clamps for engaging a bulge at the end of a neck of the container containing fluid, in which the clamps extend between the gaps of the clamps of the first tubular-shaped part in the circumferential direction and engage the same bulge of the container.

10. Medical transfer device according to claim 9, wherein:

a) the clamps of the plate have a stronger holding force than the clamps of the first tubular-shaped part, so that the plate with the spike is removed and remains with the container when removing the container from the first tubular-shaped part in use.

11. Medical transfer device according to claim 1, wherein:

a) the spike is made of synthetic material.

12. Medical transfer device according to claim 1, wherein:

a) one of the conical receiving element and the end opposite to the tip of the spike includes a filter.

13. Medical transfer device according to claim 1, wherein:

a) the cannula is made of steel.

14. Medical transfer device according to claim 1, wherein:

a) the spike is configured as a double spike and includes a channel as a ventilation channel.

15. Medical transfer device according to claim 1, wherein:

a) in use, the container for the fluid is a syringe with a receiving conical tip; and b) the conical receiving element is configured complementary to the conical receiving tip of the syringe.

16. Medical transfer device according to claim 1, wherein:

a) the cannula is configured as a double cannula and includes a channel as a ventilation channel.

17. Medical transfer device according to claim 7, wherein:

a) the clamps detachably engage the bulge.

18. Medical transfer device according to claim 1, wherein:

a) the locking mechanism includes a waling connecting plate.

* * * * *